United States Patent [19]

Peltzman et al.

[11] 4,187,153
[45] Feb. 5, 1980

[54] PRODUCTION OF ALKYLENE GLYCOLS

[75] Inventors: Alan Peltzman, New York, N.Y.; Charles C. Yang, Crosby, Tex.

[73] Assignee: Halcon Research & Development Corporation, New York, N.Y.

[21] Appl. No.: 851,025

[22] Filed: Nov. 14, 1977

[51] Int. Cl.² .............................................. B01D 3/36
[52] U.S. Cl. ........................................ 203/81; 203/91; 568/868; 568/852; 560/191; 560/248; 562/606; 562/608
[58] Field of Search ...................... 203/91, 73, 74, 81, 203/68, 69, 82, 38; 260/637 R

[56] References Cited

U.S. PATENT DOCUMENTS

| 3,262,969 | 7/1966 | Clark et al. ........................... 260/497 |
| 3,668,239 | 6/1972 | Kollar ................................. 260/497 R |
| 3,689,535 | 9/1972 | Kollar ................................. 260/497 R |
| 3,715,389 | 2/1973 | Hoch .................................. 260/497 R |
| 3,743,672 | 7/1973 | Kollar ................................. 260/497 R |
| 3,770,813 | 11/1973 | Kollar ................................. 260/497 R |
| 3,778,468 | 12/1973 | Kollar ................................. 260/497 R |
| 3,809,724 | 5/1974 | Golden ................................ 260/635 R |
| 3,872,164 | 3/1975 | Schmidt ............................... 260/497 R |
| 4,021,311 | 5/1977 | Belker ................................. 203/69 |

FOREIGN PATENT DOCUMENTS 846054 10/1977 Belgium .
888749 12/1971 Canada .
1124862 8/1968 United Kingdom .

Primary Examiner—Hiram H. Bernstein
Attorney, Agent, or Firm—William C. Long; David Dick; Jack B. Murray, Jr.

[57] ABSTRACT

According to the present invention an impure liquid containing ethylene glycol or propylene glycol, lower carboxylate esters of the glycol, water, carboxylic acid and glycol-azeotroping agent is treated for removal of substantially all of said glycol-azeotroping agent by a process which comprises distilling the impure liquid in a distillation zone to form an overheads product comprising water and glycol-azeotroping agent and a bottoms product comprising the glycol, esters and carboxylic acid, which is substantially free of said glycol-azeotroping agent, said bottoms product containing water in an amount of at least about 1 weight percent of the amount of water passed to said distillation zone with said impure liquid.

16 Claims, 2 Drawing Figures

PRODUCTION OF ALKYLENE GLYCOLS

BACKGROUND OF THE INVENTION

1. Field of the Invention

This invention relates generally to the production of polyhydric compounds and, more specifically, to an improved process for producing polyhydric compounds by hydrolysis of carboxylate esters.

2. Description of the Prior Art

Diols and triols are known compounds, many of which are produced commerically in substantial quantities. Thus, ethylene glycol and 1,2-propylene glycol (hereinafter referred to as "propylene glycol") are chemicals of acknowledged commercial importance. Ethylene glycol, for example, is used widely in the preparation of anti-freeze compositions and in the manufacture of polyester fibers. Propylene glycol finds widespread use in the manufacture of antifreeze, perfumes and solvents. Ethylene glycol manufacturing processes of commercial interest have generally been based upon ethylene oxide as a raw material. Recently, however, processes have been developed which make it possible to produce diols such as ethylene glycol and propylene glycol without the necessity for the intermediate manufacture of the epoxide. These processes employ the liquid phase reaction of the appropriate olefin, a carboxylic acid, and molecular oxygen in the presence of a catalyst to produce carboxylic acid esters of the glycol. Processes of this type are disclosed in U.S. Pat. Nos. 3,262,969; 3,668,239; 3,689,535; 3,715,389; 3,743,672; 3,770,813; 3,778,468; and 3,872,164, and in Canadian Pat. No. 888,749. The glycol can be liberated by hydrolysis of the carboxylate esters produced in such processes, and the glycol then recovered from the hydrolysis effluent. Thus, as is disclosed in U.S. Pat. Nos. 3,809,724 and 3,859,368 the carboxylate esters can be hydrolyzed with water in the presence of an acidic ion exchange resin catalyst or thermally.

The hydrolysis effluent, which normally contains the glycol, water, carboxylic acid, unreacted carboxylate esters and by-products, is then distilled generally in two successive steps, to remove water and carboxylic acid as overhead products, and the essentially water- and carboxylic acid-free liquid so produced is then treated for recovery of the desired glycol. The water so removed is generally recycled to the hydrolysis reactor and the carboxylic acid is desirably recycled to the oxidation step for use in forming additional carboxylic acid esters. Particularly efficient methods for separation of the glycol from any unconverted esters present in the liquid so treated are the azeotropic distillation processes disclosed in U.S. Pat. Nos. 3,809,724, 3,859,368 and 4,021,311, and co-pending application Ser. No. 612,825 (filed Sept. 12, 1975), now U.S. Pat. No. 4,057,471 and Ser. No. 776,392 (filed Mar. 10, 1977), now abandoned the disclosures of each of which are hereby incorporated by reference. According to these azeotropic distillation processes, a glycol-azeotroping agent (e.g., diethylbenzene, trimethylbenzene and the like) is employed to facilitate recovery of the desired glycol as overhead, which can then be treated for separation of the glycol from the glycol-azeotroping agent. The bottoms from the azeotropic distillation column contain unhydrolyzed carboxylate esters of the glycol and can be advantageously recycled to the hydrolysis reactor for formation of additional glycol therefrom. However, these bottoms can also contain small amounts of the glycol-azeotroping agent, and since the agent passes through the hydrolysis reactor substantially unaffected, glycol-azeotroping agent is present in the hydrolysis effluent. As a consequence, the subsequent successive distillation of the hydrolysis effluent to remove water and carboxylic acid results in the passage of significant amounts of the glycol-azeotroping agent into the carboxylic acid overheads product.

Since recycle to the oxidation step of a carboxylic acid stream containing substantial amounts of the glycol-azeotroping agent is highly undesirable due to the tendency of these materials to form tar-like substances during the oxidation and the attendant equipment fouling problems, the need exists to minimize the concentrations of azeotroping agent passing into the carboxylic acid overheads.

SUMMARY OF THE INVENTION

According to the present invention, an impure liquid containing ethylene glycol or propylene glycol, lower carboxylate esters of the glycol, water, carboxylic acid and glycol-azeotroping agent is treated for removal of substantially all of said glycol-azeotroping agent by a process which comprises distilling the impure liquid in a distillation zone to form an overheads product comprising water and glycol-azeotroping agent and a bottoms product containing the glycol, its esters and carboxylic acid which is substantially free of said glycol-azeotroping agent, said bottoms product containing water in an amount of at least about 1 weight percent of the amount of water passed to said distillation zone with said impure liquid.

It has been surprisingly found that distilling the impure liquid containing the ethylene glycol or propylene glycol, lower carboxylate esters of the glycol, carboxylic acid, water and glycol-azeotroping agent under conditions sufficient to remove with the overheads product only a limited amount of the water passed to the distillation zone with the liquid, allows substantially complete removal of the glycol-azeotroping agent with the overheads. Conversely, distilling the impure liquid to remove greater amounts of water as overheads results in increasingly larger amounts of glycol-azeotroping agent remaining in the bottoms product (which contains the desired glycol, carboxylate esters and carboxylic acid) and thus does not allow the production of a bottoms product which is substantially free of the glycol-azeotroping agent.

While such impure liquids have been distilled in separate steps for removal of water in a first distillation and any remaining water and carboxylic acid in a second distillation (see, e.g., U.S. Pat. Nos. 3,809,724; 3,859,368 and 4,021,311), the prior art has not recognized the criticalities which we have discovered which allow substantially complete removal of the glycol-azeotroping agent in a single distillation step.

DETAILED DESCRIPTION OF THE INVENTION

Figure 1:
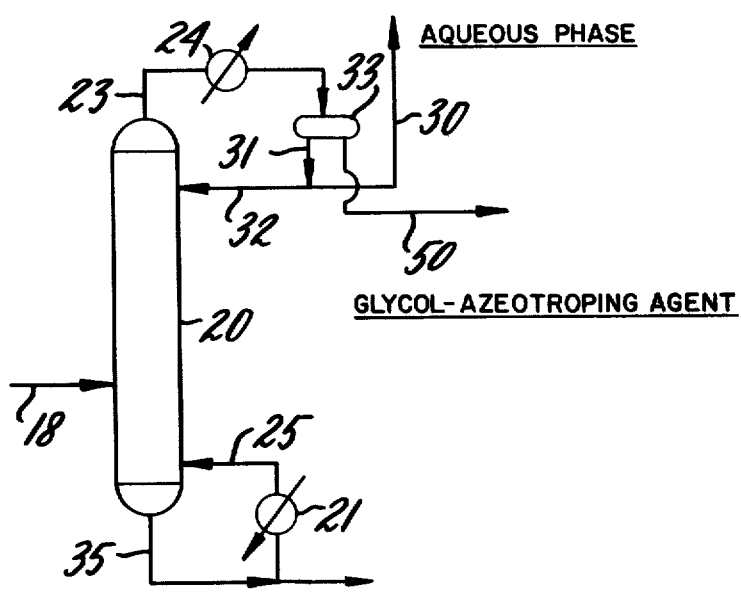
FIG. 1 is a diagrammatic illustration of one embodiment of the process of the present invention.

The composition of the impure liquid treated in accordance with the process of this invention can vary widely. Typically, however, the impure liquid will contain from about 5 to 85 weight percent, and usually from about 10 to 40 weight percent, water; up to about 50 weight percent, usually from about 1 to 30 weight percent, carboxylic acid; up to about 30 weight percent, usually from about 1 to 25 weight percent, ethylene glycol or propylene glycol; and up to about 30 weight percent, usually up to about 10 weight percent, and more usually from about 0.05 to 1.0 weight percent, of glycol-azeotroping agent, with the balance comprising lower carboxylate esters of the glycol.

The carboxylic acid present in the impure liquid is not critical and can comprise aliphatic, alicyclic, aromatic and heterocyclic monocarboxylic acids and the like. Thus, there can be suitably used a hydrocarbyl monoaliphatic acid of from 1 to 30 carbon atoms, such as formic, acetic, propionic, butyric, isobutyric, the valeric and caproic acids, as well as caprylic, capric and lauric acid, and higher monoaliphatic acids, such as myristic, palmitic, stearic, hexacosanoic and tricosanoic acid. These monoaliphatic acids may be substituted, i.e., they may contain one or more functional substituents such as lower alkoxy (methoxy, propoxy), chloro, cyano, lower alkylthio (methylthio, ethylthio, butylthio), and the like. Examples include acetoacetic, chloropropionic, cyanoacetic, methoxyacetic acid and 3-methylthiopropionic acid. Among the aromatic carboxylic acids may be mentioned benzoic, 1-naphthoic, o-toluic, m-toluic, o-chlorobenzoic, m-chlorobenzoic, p-chlorobenzoic, o-nitrobenzoic, m-nitrobenzoic, p-hydroxybenzoic, anthranilic m-aminobenzoic, p-aminobenzoic, phenylacetic, 2,4-dichlorophenyloxyacetic, hydrocinnamic, and 2-phenylbutyric acids. The alicyclic monocarboxylic acids can contain from 3 to 6 carbons in the ring, both substituted and unsubstituted, such as: cyclopropanecarboxylic, cyclopentanecarboxylic and hexahydrobenzoic. The heterocyclic acids may contain from 1 to 3 fused rings both substituted and unsubstituted, and may contain at least one and less than 4 hetero atoms such as oxygen, sulphur or nitrogen. Examples of such acids are picolinic, nicotinic, 3-indoleacetic, furoic, 2-thiophenecarboxylic, quinolinic, 2-methylindole-3-acetic, 3-chloro furoic, and 4-nitronicotinic. The carboxylic acid is preferably a lower aliphatic acid, especially acetic acid. Mixed carboxylic acids in any desired ratio can also be used.

The lower carboxylate esters of ethylene glycol or propylene glycol present can suitably comprise mono- and/or di-esters of aliphatic monobasic carboxylic acids having from 1 to 6 carbon atoms, and preferably from 2 to 4 carbon atoms, per molecule. Thus, in the preferred embodiments the lower carboxylic esters include the ethylene and propylene glycol diformates, diacetate, dipropionate, dibutyrate, diisobutyrate, divalerates and dicaproates, as well as the corresponding monoesters, and mixtures of any of the foregoing.

The "glycol-azeotroping agents" which may be present in the liquid treated in accordance with this invention are any of the azeotroping agents employed in the above-mentioned azeotropic distillation processes, i.e., U.S. Pat. Nos. 3,809,724, 3,859,368 and 4,021,311 and Ser. Nos. 612,825, and 776,392. Thus, the glycol-azeotroping agents are herein defined to include hydrocarbon azeotroping agents which are essentially water-immiscible and which form a minimum-boiling azeotrope with ethylene glycol or propylene glycol, and which have a boiling point at atmosphere pressure of from about 135° to 220° C., most preferably from about 140° to 180° C. Particularly suitable as glycol-azeotroping agents are the saturated hydrocarbons (both acyclic and cyclic), the aromatic hydrocarbons (which are for the most part alkyl-substituted benzenes), and the halogenated hydrocarbons, especially halogenated aromatic hydrocarbons. Especially preferred glycol-azeotroping agents are the trimethyl benzenes and diethyl benzenes, particularly 1,2,4-trimethyl benzene (also known as pseudocumene) and ortho-diethylbenzene, and the alkyl-substituted toluenes, particularly p-tert-butyl toluene. Suitably glycol-azeotroping agents also include ethers, ketones and alcohols. Table A below indentifies examples of glycol-azeotroping agents of this character and indicates the boiling point of the azeotrope with ethylene glycol.

TABLE A

| Glycol-Azeotroping Agent | Azeotrope b.p., °C. 760 mm. Hg | Agent b.p., °C. 760 mm. Hg |
|---|---|---|
| Ethylbenzene | 133 | 136.2 |
| Cumene | 147 | 152.8 |
| Anisole | 150.5 | 153.9 |
| Bromobenzene | 150.2 | 156 |
| 1-Bromohexane | 150.5 | 156 |
| 1,2,3-Trichloropropane | 150.8 | 156.9 |
| Propylbenzene | 152 | 159 |
| o-Chlorotoluene | 152.5 | 159 |
| 2,7-Dimethyl Octane | 153 | 160 |
| p-Chlorotoluene | 155 | 162 |
| Mesitylene | 156 | 164.6 |
| 1,3-Dibromopropane | 160.2 | 167.3 |
| 2,6-Dimethyl-4-Heptanone | 164.2 | 168 |
| Pseudocumene | 158 | 169.5 |
| Phenetole | 161.5 | 172 |
| m-Dichlorobenzene | 166 | 172 |
| 2-Octanone | 168 | 172.9 |
| Benzylmethyl Ether | 159.8 | 174 |
| Decane | 161 | 174 |
| p-Dichlorobenzene | 163 | 174 |
| Hemimellitene | 163 | 176.1 |
| Heptyl Alcohol | 174.1 | 177 |
| p-Cymene | 163.2 | 177 |
| p-Methylanisole | 166.6 | 177 |
| Bis-(2-chloroethyl) Ether | 171 | 178 |
| o-Dichlorobenzene | 165.8 | 179 |
| n-Butyl Benzene | 166.2 | 183.1 |
| 1,2-Diethylbenzene | 168 | 183.4 |
| Benzyl ethyl Ether | 169 | 185 |
| Amyl Ether | 168.8 | 187.5 |
| Phenyl propyl Ether | 171 | 190.2 |
| p-Tert.-Butyl Toluene | 173 | 193 |
| Durene | 174 | 194 |
| n-Octyl Alcohol | 184 | 195.2 |
| Isodurene | 175 | 197 |
| Acetophenone | 186 | 202 |
| Prehnitene | 176 | 204 |
| Benzyl Alcohol | 193 | 205 |
| Tetralin | 178 | 207.2 |
| Dodecane | 179 | 214.5 |
| Benzyl Acetate | 186.5 | 214.9 |
| 1,3,5-Triethyl Benzene | 183 | 215.4 |

Minimum-boiling azeotropes formed with propylene glycol and the glycol-azeotroping agents of the character above indicated generally have a slightly lower boiling point than the corresponding azeotropes formed by the glycol-azeotroping agents and ethylene glycol. Thus, with propylene glycol o-xylene forms an azeotrope boiling at 136° C., 2-octanone forms and azeotrope boiling at 169° C., 1,2,3-triethylbenzene forms an otrope boiling at 162° C., tert.-butyl benzene forms an azeotrope boiling at 155° C. and p-tert.-butyl toluene forms an azeotrope boiling at 169° C.

The temperature and pressure conditions employed in distillation of the impure liquid in accordance with the process of this invention can vary widely, and will, of course, depend on the precise composition of the impure liquid to be distilled, the degree of removal of the glycol-azeotroping agent desired and a variety of other factors. Generally, however, the distillation is effected at a pot temperature of from about 50° to 170° C., usually from about 120° to 160° C., and at a pressure of from about 1 to 70 psia, usually from about 2 to about 25 psia, although higher or lower temperatures and/or pressures can of course be employed.

The number of theoretical vapor/liquid contacting stages employed in such distillation to achieve the required separation of water and glycol azeotroping agent as overheads product can also vary widely and will also depend on the precise impure liquid composition and the degree of removal of the glycol-azeotroping agent desired, as well as on a variety of other factors, which will be obvious to the skilled practitioner. Thus, one skilled in the art could easily ascertain the optimum number of such theoretical stages necessary to effect treatment of a particular impure liquid in accordance with the process of the present invention. Generally, however, at least about 2, and usually at least about 4, theoretical vapor/liquid contacting stages will be employed above the feed of the impure liquid to the distillation zone, and at least about 4, and usually at least about 6, theoretical vapor/liquid contacting stages will be employed below such feed point.

The reflux ratio employed in practice of the process of the present invention is also not critical, and can be easily ascertained by one having ordinary skill in the art for treatment of a given impure liquid, considering such factors as the liquid's composition, the type of distillation apparatus employed and the degree of removal of glycol-azeotroping agent desired. Generally, a reflux ratio of at least about 0.1:1, and preferably at least about 0.2:1 will be employed.

The liquid obtained by the process of this invention following distillation will be removed as bottoms product from the distillation zone and will generally contain less than about 500 ppm by weight, preferably less than about 250 ppm by weight, and more preferably less than about 10 ppm by weight glycol-azeotroping agent. For purposes of this invention the liquid bottoms so produced is said to be "substantially free" of glycol-azeotroping agent when the concentration of such agent in the bottoms product so obtained is less than about 500 ppm by weight.

As has been pointed out above, the surprisingly facile recovery of substantially all glycol-azeotroping agent from the impure liquids treated in accordance with the present invention is found to result when the quantity of water taken as overheads in the distillation column is limited, that is, incomplete removal of the water content of the impure liquid passed to the distillation zone is required in order to allow removal of the maximum amount of the undesired glycol-azeotroping agent. The amount of water not so removed, expressed as a weight percent of the water passed to the distillation zone with the impure liquid, is herein termed the "bottoms water split", which in a continuous process is calculated on the basis of impure liquid treated per unit time and which in a batch process is calculated on the basis of the total quantity of impure liquid heated during the batch operation. The minimum bottoms water split required for maximum removal of glycol-azeotroping agent in accordance with this invention from a particular impure liquid containing the same, of course, varies depending upon such factors as the particular glycol-azeotroping agent sought to be removed, the amount of such agent in the impure liquid, the relative concentrations of water, carboxylic acid, ethylene glycol or propylene glycol and its esters in impure liquid esters, and a variety of other factors. However, a bottoms water split of at least about 1 weight percent, more preferably, at least about 1.5 weight percent, will generally be required in order to achieve bottoms product substantially free of glycol-azeotroping agent.

Most preferably, the bottoms product so obtained contains at least about 0.1 weight percent water, and still more preferably at least about 0.3 weight percent water.

The bottoms product obtained from the distillation zone employing the process of this invention can be treated in conventional manner for removal of carboxylic acid and any remaining water therefrom, and for treatment of the resulting substantially water- and carboxylic acid-free glycol/ester liquid for separation and recovery of the desired ethylene glycol or propylene glycol and its carboxylate esters.

A discussion of the adjustment of the distillation operating conditions (e.g., temperature, pressure, liquid reflux, number of theoretical vapor/liquid contacting stages, feed rates and rates of overheads and bottoms product withdrawal) necessary to achieve the desired bottoms water split, and hence maximum removal of glycol-azeotroping agent, in a particular distillation apparatus is not necessary to a complete understanding of the practice of the art of this invention and, as with any conventional distillation, can be achieved by known means. Thus, such operating conditions can be independently or cooperatively adjusted, consistent with the degrees of freedom of the system and following conventional distillative methods. For example, at steady-state distillation conditions in a continuous process, the reboiler temperature of a conventional distillation column can be decreased (by reducing the temperature of the heat source thereto) to decrease the quantity of water vaporised in the column from impure liquid fed thereto and thereby increase the bottoms water split for the column and improve the efficiency of the column in removing the undesired glycol-azeotroping agent in accordance with the process of the invention.

Figure 2:
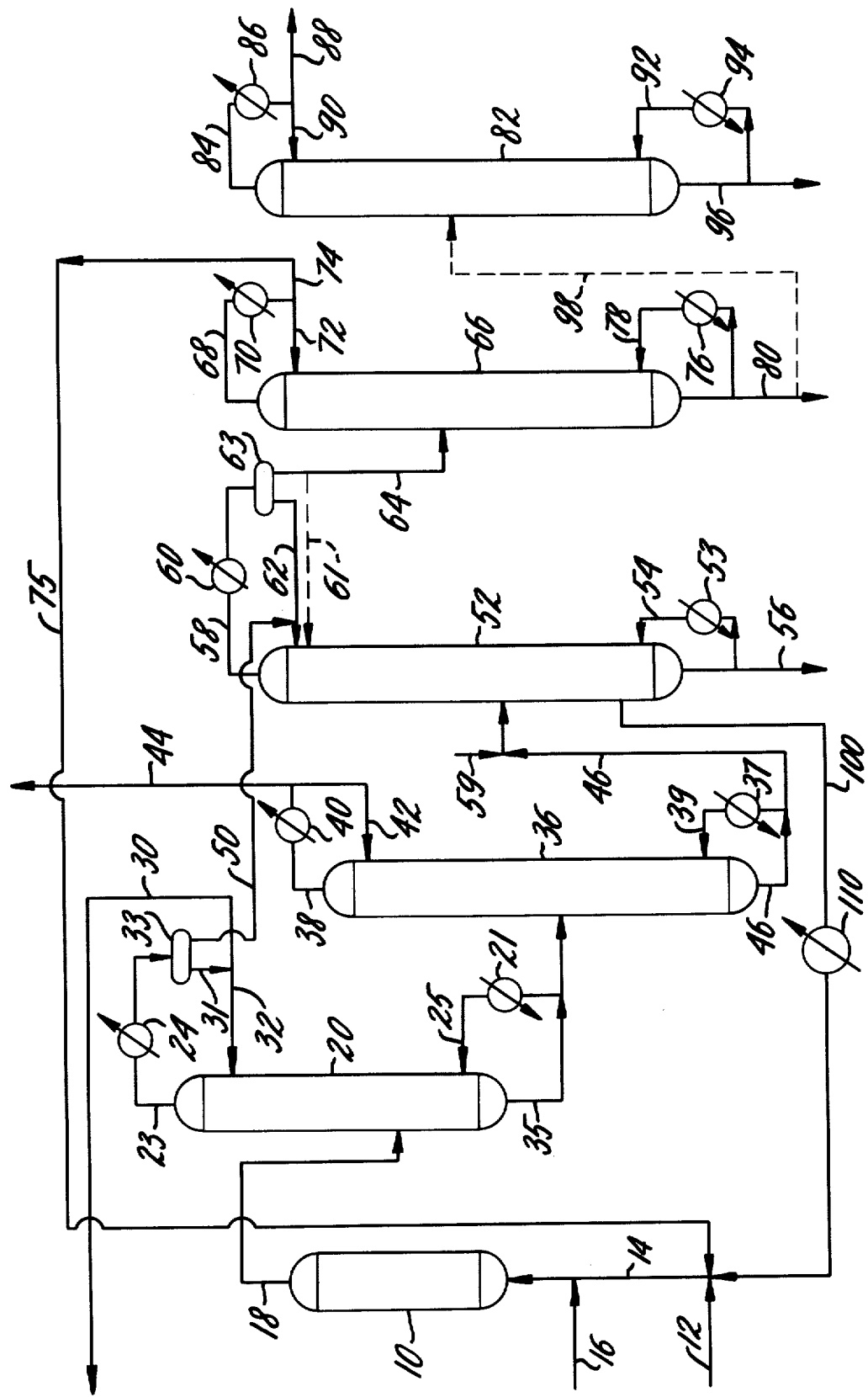
FIG. 2 is a diagrammatic illustration of an overall system in which the process of FIG. 1 is integrated with an ethylene glycol hydrolysis and azeotropic distillation recovery method.

There follows a detailed description of the use of our process in combination with such a hydrolysis and azeotropid distillation operation. In the following discussion of the invention, the process will be described and exemplified with particular reference to ethylene glycol and its carboxylate esters, especially ethylene glycol mono- and di-acetates, but the process is equally applicable to propylene glycol and its esters, the discussion in terms of ethylene glycol and its esters being solely for convenience and ease of description. As illustrated in FIGS. 1 and 2, the process is practiced in a continuous manner, although it will be understood that our process can also be practiced in a batchwise or semi-continuous manner.

Referring now to the drawings, wherein like numerals refer to the same or similar element, there is illustrated one embodiment of the process of this invention wherein an impure liquid containing ethylene glycol, lower carboxylate esters of the glycol (e.g., a mixture of ethylene glycol monoacetate and diacetate), monocarboxylic acid (e.g., an acetic acid), water and glycol-azeotroping agent (e.g., an alkyl-substituted benzene such as 1,2,4-trimethylbenzene) is passed via line 18 to distillation column 20 which is provided with a reboiler 21, or other heating means, a condenser 24, and a phase separator 33. In column 20, water and glycol-azeotroping agent present in the impure liquid are vaporized and, along with a small amount of carboxylic acid also vaporized, are withdrawn through line 23 and passed to condenser 24, which can comprise either a partial or total condenser, the latter being the type illustrated.

The condensate is passed to phase separator 33 wherein the water and carboxylic acid form one phase and the glycol-azeotroping agent forms a second phase, the latter being withdrawn from separator 33 through line 50. The aqueous phase is withdrawn through line 31, with part of it being returned to column 30 through line 32 as reflux and the remainder being withdrawn through line 20. The portion of the impure liquid supplied to column 20 which is not vaporized and withdrawn through line 23 and which comprises ethylene glycol, carboxylic acid, monoesters and diesters of ethylene glycol and water, and which is substantially free of glycol-azeotroping agent, is withdrawn as bottoms product through line 35 and a portion thereof is recycled via line 25 and reboiler 21 to column 20. The remaining bottoms can be treated, if desired, for recovery of ethylene glycol and its esters therefrom.

As stated previously, the process of this invention for removal of glycol-azeotroping agents from such impure liquids is particularly adapted for use in processes for preparing ethylene glycol or propylene glycol in which the lower carboxylate esters of such glycols are hydrolyzed and in which the glycol is sought to be recovered by an azeotropic distillation process.

Referring then to FIG. 2, an ester feed stream is passed via lines 12 and 14 to hydrolysis reactor 10. Water for the hydrolysis enters through line 16 and is combined with the hydrolysis ester feed in line 14 before entering reactor 10.

The ester feed comprises a mixture of lower carboxylate monoesters and diesters of ethylene glycol (i.e., esters of ethylene glycol), water, and a monocarboxylic acid, e.g., a hydrocarbyl monocarboxylic acid having from 1 to 6 carbon atoms per molecule, and preferably having from 1 to 4, and most preferably 1,2 or 3, carbon atoms per molecule. Suitable acids therefore include formic acid, acetic acid, propionic acid, butyric acid, isobutyric acid, and the valeric and caproic acids. Accordingly, the lower carboxylate monesters of ethylene glycol include ethylene glycol monoformate, ethylene glycol monoacetate, ethylene glycol monopropionate, ethylene glycol monobutyrate, the ethylene glycol monovalerates and the ethylene glycol monocaproates, and the diesters include the corresponding diesters of the same alkanoic acids. Mixtures of ethylene glycol monoformate, ethylene glycol monoacetate, monopropionate, monobutyrate and monoisobutyrate, the corresponding diesters, and mixtures of such monoesters and such diesters, are typical feedstocks and the diacetate-monoacetate mixtures are particularly typical feedstocks. Mixtures of esters such as mixtures of ethylene glycol monoacetate and ethylene glycol monopropionate, as well as mixtures with one or more diesters, including mixed diesters such as ethylene glycol acetate propionate, can also be used. As used herein, therefore, the term "ester feed" is intended to include not only the lower carboxylate ethylene glycol monoesters alone or the ethylene glycol diesters alone but also mixtures of monoester-diester mixtures and mixed esters, as well as with mixtures of different ehtylene glycol carboxylate esters, in any proportion.

The ester feed to the hydrolysis operation can comprise the effluent from a reaction which produces ethylene glycol monoester or ethylene glycol diester, or mixtures of the two. Typical reaction effluents of this nature are described, for example, in the above-mentioned U.S. Pat. No. 3,689,535, wherein monoester is produced in the presence of substantial quantities of the diester and in British Pat. No. 1,124,862, wherein the production of monoester substantially free from diester is disclosed. The hydrolysis step can be applied to glycol esters produced in any manner, whether by the process of the above U.S. patent or the British patent or by various other processes.

In effecting the hydrolysis, the ethylene glycol lower carboxylate ester, or ester mixture, is suitably heated in the presence of water until at least some hydrolysis has occurred. Although the hydrolysis reaction will take place solely under the influence of heat, it may be preferred, in order to increase the rate of reaction, to effect hydrolysis in the presence of small amounts of an acidic hydrolysis catalyst, such as a mineral acid, e.g., sulphuric acid and phosphoric acid, but most preferably a solid catalyst, e.g., in the form of any of the conventional acidic ion exchange resins, is employed, as described in the previously-mentioned U.S. Pat. No. 3,809,724. Thus, the hydrolysis catalyst can be used in the form of beds through which the feed to be hydrolyzed can be continuously passed. Typical examples of suitable ion exchange resins include cation exchange resins of the sulfonic acid type, such as the polystyrene sulfonic acids, which can be exemplified by commercial products sold under the names Dowex-50, Dowex-50W, Duolite C-20, Ionac C-249, Amberlite IR-120, Amberlyst 15 and Dowex MSC-1.

The hydrolysis step is thus suitably carried out by causing the glycol ester or ester mixture to react under the influence of heat (with or without a catalyst) to liberate (i.e., hydrolyze) from 15 to 80 mol percent of the acyl moieties, e.g., acetate moieties, as lower carboxylate acid, e.g., acetic acid. At the same time ethylene glycol is liberated. Generally, it is desirable to use at least 0.25 mol of water per equivalent of acyl moiety present in the hydrolysis feed. Preferably, the amount of water added is in the range of from about 0.75 to 5 moles of water per equivalent of acyl moiety. Of course, greater amounts of water can be used, for example up to 20 moles per equivalent of acylmoiety, but the use of such large amounts of water is both unnecessary and economically disadvantageous.

Hydrolysis reaction temperatures of at least about 50° C. are generally employed in order to obtain economically satisfactory rates of hydrolysis, but when catalysts are employed, temperatures as low as 25° C. can be satisfactorily used. Reaction temperatures above about 250° C. are generally not desired however, since at higher temperatures thermal degradation of the resin can become significant. Preferably temperatures of about 50° C. to about 200° C. are employed. Pressure is not in any manner critical to the conduct of the hydrolysis as long as it is sufficient at the prevailing temperature to keep at least a portion of the reaction mixture in the liquid phase. Thus, pressures of as little as 50 mm Hg can be employed as also can pressures of several thousand psia. Residence time of reactants and products within the hydrolysis zone is in no way critical to this invention and any practically obtainable residence times are suitable. Thus, for example, residence times from as little as 1 minute up to and including several hours, e.g., 4 hours, or longer are entirely feasible.

Hydrolysis effluent, which contains carboxylic acid (e.g., acetic acid), water, ethylene glycol, monoesters and diesters of ethylene glycol, and glycol-azeotroping agent, is withdrawn from hydrolysis reactor 10 via line 18 and is introduced into water distillation column 20 of FIG. 1 wherein the hydrolysis effluent is distilled in accordance with the improved process of this invention as described above for recovery of glycol-azeotroping agent and water as overhead product. The portion of the aqueous phase withdrawn from separator 33 which is not refluxed to column 20 via conduit 32 can be suitably recycles via conduit 30 to conduit 16 and thence into hydrolysis reactor 10.

The bottoms product which is withdrawn from column 20 and which comprises the ethylene glycol-containing liquid which is substantially free of glycol-azeotroping agent is passed as feed to distillation column 36, also provided with appropriate heating means (e.g., a reboiler 37), wherein water and carboxylic acid are vaporized. The vapors so produced are withdrawn through line 38 and condensed in condenser 40 with some of the condensate being returned to column 36 as reflux through line 42 and the remainder being withdrawn from the system through line 44.

The distillation steps to vaporize water and carboxylic acid in column 36 can be carried out over a wide range of conditions, although it has been found preferable to operate at pot temperatures of from about 120° C. to 240° C. and at pressures of from about 300 to about 3500 mm Hg. The reflux ratios and the number of theoretical vapor liquid contacting stages employed in column 36 can also vary widely and can be easily ascertained by the skilled practitioner. It will be understood, however, that operation outside the above-mentioned temperature and pressure ranges is possible and the choice of specific combinations of conditions is entirely within the scope of persons skilled in the art.

The manner in which the bottoms product withdrawn (via line 46) from column 36 is treated for recovery of ethylene glycol is not critical to the process of the present invention. Thus, these bottoms can be treated employing any of the azeotropic distillation methods disclosed in U.S. Pats. Nos. 3,809,724, 3,859,368 and 4,021,311, and Ser. Nos. 612,825 and 776,392, i.e., distillation in the presence of a glycol-azeotroping agent which both forms a minimum-boiling azeotrope with ethylene glycol and is essentially water-immiscible. The minimum-boiling azeotrope is withdrawn from the distillation zone as overhead, and the overhead is separated into a first phase comprising the azeotroping agent (which can be recycled to the distillation zone) and a second phase comprising the desired glycol. The glycol is then recovered from the second phase, e.g., by distillation, extraction or other appropriate means.

In the embodiment illustrated in FIG. 2, the essentially water-and carboxylic acid-free liquid containing the glycol and its esters is withdrawn from column 36 through line 46 and can be introduced as ester feed to azeotropic distillation column 52, which, in the embodiment illustrated, is a distillation column suitably provided with heating means, e.g., a convenient reboiler 53, and with a bottoms withdrawal line 56 and an overhead vapor line 58, the latter being connected to a condenser 60. The condensate (comprising the ethylene glycol azeotrope with the glycol-azeotroping agent) which is in condenser 60 flows to a phase-separator 63, and the condensed glycol-azeotroping agent is returned to column 52 through line 62 as reflux, whereas the ethylene glycol phase is withdrawn through line 64 and is introduced into a refining column 66, also provided with a heating means, suitably in the form of a reboiler 76. A portion of the ethylene glycol phase may be returned to zone 52 as reflux if desired via line 61, as disclosed in Belgian Pat. No. 846,054, the disclosure of which is incorporated herein by reference. The minimum reflux ratio of the glycol-containing phase is typically 0.3:1, preferably 0.5:1, and most preferably 1:1. From a practical standpoint the reflux ratio of the glycol-containing phase is generally not above 8:1 although it can be higher if desired. Preferably, all of the phase containing the glycolazeotroping agent is returned to the distillation column as reflux. When both the glycol-azetoroping agent and the product glycol are refluxed to the distilation zone in this manner there is a significant improvement in the purity of the glycol removed as distillate.

In column 66, ethylene glycol ester and glycol-azeotroping agent contained in the ethylene glycol phase withdrawn from phase separator 63 is removed as vapor through line 68, and ethylene glycol in substantially purified form is withdrawn as bottoms through line 80. The vapors in line 68 are condensed in condenser 70 and a portion is returned as reflux to column 66 through line 72 and the remainder is withdrawn through line 74. Portions of the material in line 61 can, if desired, be combined with the feed to column 52, and make-up glycol-azeotroping agent, as required, can be added through line 59 or added to line 62. Preferably, the purified ethylene glycol withdrawn through line 80 is given a final distillation to insure against the presence in the product of higher boiling materials such as diethylene glycol and the like, which may tend to form in small amounts. Thus, if this further distillation is desired, the ethylene glycol from line 80 is passed through line 98 into distillation column 82 which is operated at pot or reboiler temperature of from about 120° to 210° C. and pressures of from about 50 mm Hg to 7 psig to remove purified glycol through line 84 leading to condenser 86, the condensate from which is partially returened to column 82 as reflux through line 90, and the remainder of which is withdrawn as product glycol through line 88. The heavier components separated by the distillation are removed through line 96. The reboiler 94 in line 92 provides the necessary heat for maintenance of the distillation.

To complete the integration of the azeotropic distillation system with the hydrolysis system, a line 75 connects with line 74 to conduct the withdrawn condensate containing glycol-azeotroping agent from column 66 to the feed to hydrolysis zone 10 and a side steam from column 52 comprising vapors of lower carboxylate esters of ethylene glycol is withdrawn through line 100 and also combined with the feed of the hydrolysis zone, after being condensed by condenser 110.

When the ethylene glycol content of the bottoms withdrawn from column 36 is relatively low, e.g., below 10 mol percent, and when these bottoms contain meaningful amounts of lower carboxylate monoester of ethylene glycol, e.g., at least 15 mol percent, it is advantageous to effect a disproportionation of the monoester as described in the above-mentioned U.S. Pat. No. 3,859,368, in which the lower carboxylate monoesters of alkylene glycols such as ethylene glycol, in the presence of a weak base catalyst and without the need for the presence of an extraneous reactant, undergo what is characterized as a disproportionation reaction to produce ethylene glycol and the corresponding lower carboxylte diester of ethylene glycol.

It will be obvious from a reading of the foregoing disclosure that hydrolysis reactor 10 can be configured to employ a downwardly flowing feed, so that the combined water and ester feed flows downwardly through reactor 10 and hydrolysis effluent would then be withdrawn from the lower portion of the reactor.

The vessels employed in the improved process of this invention are conventional and their materials of construction are not critical to the practice of this invention, although materials which are resistant to acid attack and resulting corrosion in such acidic media are economically preferred.

The following examples of application will serve to give a more full understanding of the invention, but it will be understood that these examples are illustrative only and are not intended as limiting the invention. All parts are by weight unless otherwise indicated.

EXAMPLE 1

In a series of runs, a liquid containing 11.5 weight percent water, 18.5 weight percent acetic acid, 20.2 weight percent ethylene glycol diacetate (EGDA), 34.5 weight percent ethylene glycol monoacetate (EGMA), 13.5 weight percent ethylene glycol (EG), and 1.8 weight percent ortho-diethyl benzene (ODEB) is passed at a rate of about 2,000 parts per hour to an Oldershaw distillation column consisting of 5 theoretical plates of 2-inch in diameter above the feed point and 12 theoretical plates of 2-inch in diameter below the feed point and provided with a 1500 cc reboiler. The column is also provided with a total condenser and a Dean-Stark tube. In operation, overhead vapors are condensed in the condenser and the condensed two-phase liquid is decanted in the Dean-Stark tube. Employing an overhead pressure of about 150 mmHg, a reflux ratio of 0.7, and the selected bottoms temperature, maintained by means of the reboiler, the liquid so introduced is distilled in the column in each run to determine the effect of the bottoms water split upon the concentration of the glycol-azeotroping agent in the withdrawn bottoms product.

In each run, after steady state conditions are reached, the liquid phases obtained by decanting of the condensed overheads and the bottoms product are analyzed, the data so obtained being set forth in Table 1 below.

TABLE 1

| Run No. | Bottoms Temp. (°C.) | Percent of Feed Taken as: | | Overhead Product* | | Bottoms Product* | |
|---|---|---|---|---|---|---|---|
| | | Overheads | Bottoms | $H_2O$ | ODEB | $H_2O$ | ODEB |
| 1 | 126 | 26 | 74 | 95 | 83.3 | 5 | 16.7 |
| 2 | 110 | 21 | 79 | 90 | 98.7 | 10 | 1.3 |
| 3 | 100 | 16 | 84 | 83 | 99.6 | 17 | 0.4 |

*Expressed as weight percent of component passed to the distillation column with the feed.

The concentrations of water and ODEB in the bottoms product expressed as weight percent of the total bottoms product, are determined to be as follows:

TABLE 2

| Run No. | Weight Percent in Bottoms Product: | |
|---|---|---|
| | $H_2O$ | ODEB |
| 1 | 0.7 | 0.04 |
| 2 | 0.84 | 0.03 |
| 3 | 2.1 | 0.009 |

Therefore, it can be seen that by increasing the concentration of water in the bottoms by about 200 percent, a bottoms product is obtained having a concentration of the glycol-azeotroping agent which is over 340 percent lower than the concentration in the bottoms in the initial run.

EXAMPLE 2

The procedure of Example 1 is repeated except that the distillation column consists of 5 theoretical trays of 2-inch in diameter above the feed point and 10 theoretical trays of 2-inch in diameter below the feed point, the glycol-azeotroping agent comprises 1,2,4-trimethyl benzene (TMB) and the column is operated at an overhead pressure of about 340 mmHg and employs a reflux ratio of about 0.3.

The data thereby obtained is set forth in Table 3 below:

TABLE 1

| Run No. | Bottoms Temp. (°C.) | Percent of Feed Taken as: | | Bottoms Product* | | Product* | |
|---|---|---|---|---|---|---|---|
| | | Overheads | Bottoms | $H_2O$ | TMB | $H_2O$ | TMB |
| 1 | 158 | 25 | 75 | 99.9 | 98 | 0.1 | 2 |
| 2 | 142 | 20 | 80 | 98.5 | 99.97 | 1.5 | 0.03 |
| 3 | 125 | 15 | 85 | 95 | 100 | 5 | 0 |

*Expressed as weight percent of the component passed to the distillation column with the feed.

The concentrations of water and TMB in the bottoms product, expressed as weight percent of the total bottoms product, are determined to be as follows:

TABLE 4

| Run No. | Weight Percent in Bottoms Product: | |
|---|---|---|
| | $H_2O$ | TMB |
| 1 | 0.05 | 0.5 |
| 2 | 0.3 | 0.0005 |
| 3 | 2 | nil≠ |

(≠ -Level of sensitivity of method of detection = 1 ppm)

As can seen from Tables 3 and 4 above, Run No. 1, in which the "bottoms water split" is 0.1 weight percent results in an unacceptably high concentration of TMB in the bottoms product, namely, 5,000 ppm, and thus represents a comparative run to Runs 2 and 3, in which the process of the present invention is illustrated for obtention of the bottoms product substantially free of glycol-azeotroping agent. As is shown in Runs 2 and 3, a "bottoms water split" of 1.5 and 5 weight percent, respectively, results in bottoms products containing TMB in concentrations of 5 ppm and no detectable TMB, respectively.

It will be obvious that various changes and modifications may be made without departing from the invention and it is intended, therefore, that all matter contained in the foregoing description shall be interpreted as illustrative only and not limitative of the invention.

We claim:

1. In a process for removing glycolazeotroping agent from an impure liquid containing the same, said impure liquid also containing ethylene glycol or propylene glycol, lower carboxylate esters of the glycol, carboxylic acid and water wherein said impure liquid is subjected to distillation in a distillation zone to produce an overhead product containing water and glycol-azeotropic agent and a bottoms product containing said glycol, esters and carboxylic acid, the improvement which comprises producing a bottoms product which is substantially free of said glycol-azeotropic agent, by conducting said distillation under conditions sufficient to maintain in said bottoms product a water concentration of at least about 1 weight percent.

2. The improved process according to claim 1 wherein the glycol-azeotroping agent comprises a member selected from the group consisting of hydrocarbons which are essentially water-immiscible and which form a minimum-boiling azeotrope with the glycol, and which have a boiling point at atmospheric pressure of from about 135° to 220° C.

3. The improved process of claim 1 wherein the carboxylic acid comprises a member selected from the group consisting of mono-aliphatic acids of from 1 to 30 carbon atoms.

4. The improved process according to claim 1 wherein the lower carboxylate esters of the glycol comprise at least one member selected from the group consisting of mono- and di-esters of aliphatic monobasic carboxylic acids having from 1 to 6 carbon atoms per molecule.

5. The improved process according to claim 1 wherein said bottoms product contains water in an amount of at least about 1.5 weight percent of the amount of water passed to said distilation zone with said impure liquid.

6. The improved process according to claim 1 wherein the glycol-azeotroping agent comprises a member selected from the group consisting of alkyl-substituted benzenes and alkyl-substituted toluenes.

7. The improved process according to claim 6 wherein the glycol-azeotroping agent comprises a member selected from the group consisting of trimethyl benzenes and diethyl benzenes.

8. The improved process according to claim 7 wherein the glycol-azeotroping agent is 1,2,4-trimethyl benzene or ortho-diethyl benzene.

9. The improved process according to claim 1 wherein the glycol comprises ethylene glycol and said distillation is effected at a bottoms temperature of from about 50° to 170° C.

10. The improved process according to claim 1 wherein the glycol comprises ethylene glycol and the distillation is effected at a pressure of from about 1 to 70 psia.

11. The improved process according to claim 1 wherein the bottoms product so produced contains glycol-azeotroping agent in a concentration of less than about 250 ppm by weight.

12. The improved process according to claim 1 wherein the glycol is ethylene glycol, the carboxylic acid comprises a hydrocarbyl monoacarboxylic acid having from 1 to 6 carbon atoms per molecule, the glycol-azeotroping agent comprises a member selected from the group consisting of alkyl-substituted benzenes and alkyl-substituted toluenes, and said distillation is effected at a bottoms temperature of from about 50° to 170° C. and a pressure of from about 1 to 70 psia, thereby forming as bottoms product a liquid containing glycol-azeotroping agent in a concentration of less than about 250 ppm by weight.

13. The improved process according to claim 1 wherein the bottoms product contains glycol-azeotroping agent in a concentration of less than about 10 ppm by weight.

14. The improved process according to claim 1 wherein the carboxylic acid comprises a member selected from the group consisting of mono-aliphatic acids or from 1 to 6 carbon atoms.

15. The improved process according to claim 1 wherein said bottoms product contains at least about 0.1 weight percent water.

16. In a process for distilling an impure liquid containing glycol-azeotroping agent, ethylene glycol or propylene glycol, lower carboxylate esters of the glycol, carboxylic acid and water to remove water and carboxylic acid therefrom wherein:

(a) the impure liquid is subjected to distillation in a first distillation zone to produce a first overhead product comprising water and glycol-azeotroping agent and a first bottoms product comprising said glycol, esters and carboxylic acid; and (b) said first bottoms product is subjected to distillation in a second distillation zone to produce a second overhead product comprising carboxylic acid and a second bottoms product containing said glycol and esters, the improvement which comprises conducting said first distillation under conditions sufficient to provide in said first bottoms product a water concentration of at least about 1 weight percent, thereby effecting substantially complete removal of said glycolazeotroping agent in said first distillation with the first overhead product and thereby forming a first bottoms product which is substantially free of said glycol-azeotroping agent so as to minimize the quantity of said glycol-azeotroping agent which is introduced to said second distillation zone with said first bottoms product.

* * * * *